(12) United States Patent
Smith et al.

(10) Patent No.: US 7,263,393 B2
(45) Date of Patent: Aug. 28, 2007

(54) BIOFEEDBACK RING SENSORS

(75) Inventors: Kurt Smith, Boulder, CO (US);
Corwin Bell, Boulder, CO (US); Jan Delaney, Longmont, CO (US); Todd Gilbreath, Houston, TX (US); Ehsan Alipour, Green Brae, CA (US);
Timothy Nutt, San Francisco, CA (US); Eric Edward Schultz, Palo Alto, CA (US)

(73) Assignee: Healing Rhythms, LLC., Boulder, CO (US)

( * ) Notice: Subject to any disclaimer, the term of this patent is extended or adjusted under 35 U.S.C. 154(b) by 303 days.

(21) Appl. No.: 10/863,029

(22) Filed: Jun. 7, 2004

(65) Prior Publication Data

US 2005/0272986 A1 Dec. 8, 2005

(51) Int. Cl.
*A61B 5/00* (2006.01)
*A61B 5/05* (2006.01)

(52) U.S. Cl. ...................... 600/310; 600/547

(58) Field of Classification Search .............. 600/310, 600/322, 323, 340, 344, 382, 384, 386, 499, 600/503, 546, 547; 128/905; 63/15.45, 63/15.5, 15.7
See application file for complete search history.

(56) References Cited

U.S. PATENT DOCUMENTS

| 5,501,384 A | * | 3/1996 | Wisniewski | .................. 224/539 |
| 6,353,750 B1 | * | 3/2002 | Kimura et al. | .............. 600/344 |
| 2002/0188205 A1 | * | 12/2002 | Mills | .......................... 600/481 |

* cited by examiner

*Primary Examiner*—Eric F Winakur
(74) *Attorney, Agent, or Firm*—Holland & Hart LLP

(57) ABSTRACT

The present invention provides a novel ring type sensor for measuring biometric information. The ring sensor includes a rest for an appendage and a wing pivotally connected to the rest. A biasing member supplies a compressive force to the wing (relative to the rest) such that an appendage from which biometric information is to be measured is snuggly held by the rest and the wing.

35 Claims, 7 Drawing Sheets

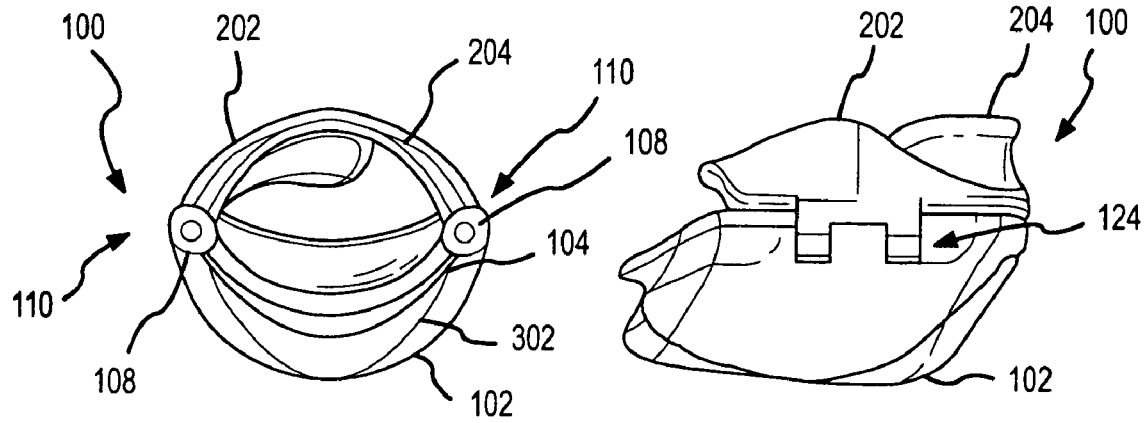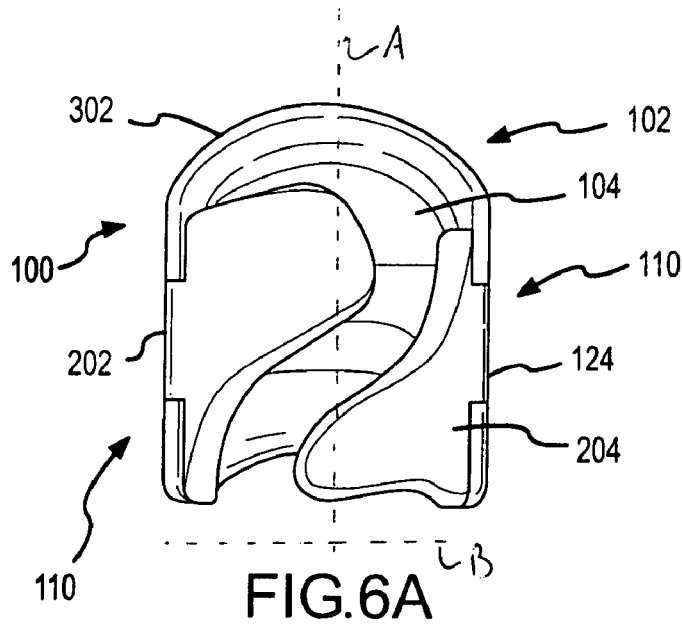
FIG.6C  FIG.6B  FIG.6A

BIOFEEDBACK RING SENSORS

FIELD OF THE INVENTION

The present invention relates to biofeedback sensors and, more particularly, to biofeedback ring sensors.

BACKGROUND OF THE INVENTION

Biofeedback sensors provide information about physiological aspects of a person. In some biofeedback sessions, the client sits in a chair or lays on a couch or bed. Sensors are attached to the client's skin at various locations on the body, such as, for example, the shoulders, fingers, back, and head. Electrical signals or impulses from these locations are used to provide visual or auditory feedback reflecting various information. Other variations on biofeedback sessions are possible, with the above being an exemplary type of biofeedback session for background purposes.

Some biofeedback sensors are simple electrodes attached to the client using an adhesive tab with an electrical contact or electrode. These adhesive tabs are placed in the desired locations on the client with the electrode between the client's skin and the tab. The electrode sensors are good measures of electrical information, such as epidural skin response, which is a measure of skin resistance and useful for measuring stress or the like, the use of adhesives on the client can result in an unpleasant removal experience. Sometimes the simple electrode sensor is attached to a VELCRO strip and wrapped around an appendage, such as, for example, a finger.

Another type of biofeedback sensor is an infrared sensor. Infrared sensors generally are not used to determine skin electrical responses, but may be used to determine other biometric information, such as, heart rate, blood pressure, blood oxygen levels, or the like. Although infrared sensor can be place on the client using an adhesive tab, they are more typically located by locating the infrared sensor on the client, and wrapping tape, VELCRO® straps, an elastic bandage, or the like around the client and the sensor to locate the infrared sensor. Again, while the sensor is adequate for measuring the biometric information, using tape, VELCRO® straps or the like leaves much to be desired. Frequently, the attachment devices wear out requiring frequent replacement.

Some infrared sensors are loaded in clip style devices, such as, for example, an ear clip or a finger clip. While these clips work somewhat better than the attachment devices above, they are frequently bulky and not well suited for all individuals.

Thus, it would be desirous to develop and improved finger sensor to read biometric information.

SUMMARY OF THE INVENTION

The present invention provides an improved finger sensor. The improved finger sensor comprises an appendage rest with a sensor coupled to the apparatus such that when an appendage of a client is in the appendage rest, the sensor measures biometric information. A cover or wing pivotally connected to the apparatus is attached to a biasing member that provides a compressive force to the appendage tending to snuggly contain the appendage in the appendage rest with the wing.

The present invention also provides a system for obtaining a plurality of biometric information using a plurality of sensors. Each of the sensors comprises an appendage rest and a cover pivotally connected to the appendage rest. The pivotal connection includes means for causing the cover to snuggly hold an appendage of the user in the appendage rest such that a plurality of sensors measures biometric information.

The foregoing and other features, utilities and advantages of the invention will be apparent from the following more particular description of a preferred embodiment of the invention as illustrated in the accompanying drawings.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

FIG. 6A-6C show a top plan view, a side elevations view, and a front elevation view of the biofeedback sensor of FIG. 1;

DETAILED DESCRIPTION

The present invention will be explained with specific reference to FIGS. 1 to 8. It is to be understood that the drawings are diagrammatic and schematic representations of particular embodiments of the present invention, and are not limiting, nor are they drawn to scale. Further, while the present invention is described in relation to a finger sensor, the sensor could be placed in other locations, such as a toe or the like. Finally, while the present invention is described using an electrode and/or an infrared biofeedback sensor, one of ordinary skill in the art would recognize on reading the disclosure that other types of biofeedback sensors could be used.

Figure 1:
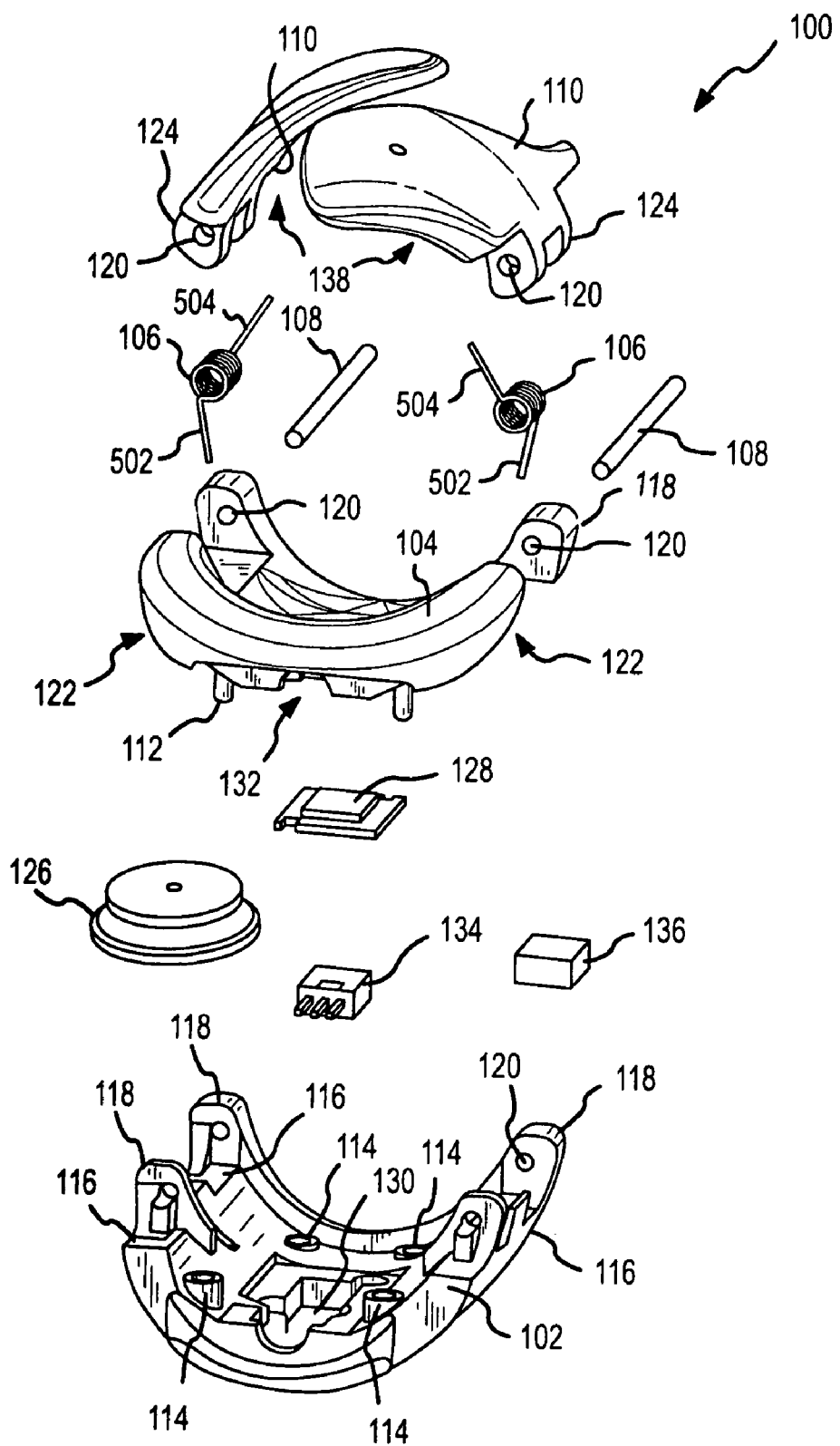
FIG. 1 is an exploded view of a biofeedback sensor constructed in accordance with an embodiment of the present invention.

Referring first to FIG. 1, an exploded view of a biofeedback sensor 100 is shown. Biofeedback sensor 100 includes a bottom 102, a finger rest 104, a pair of elastic biasing members 106, such as the springs as shown, pins 108, and a pair of top wings 110 or panels. While shown with two elastic biasing members 106 and two top wings 110, biofeedback sensor 100 could be constructed with one elastic biasing member 106 and top wing 110, but it is believed using two wings 110 provides a better fit and aesthetic design.

As shown, bottom 102 is coupled to finger rest 104 by pegs 112 on finger rest 104 frictionally engaging holes 114 on bottom 102. Pegs 112 could be replaced by through holes 702, and holes 114 could be threaded holes 704 such that screws 706 could be inserted through through holes 702 and threaded into threaded holes 704.

Bottom rest 102 has a plurality of shoulders 116 and a plurality of alignment tabs 118 with a pin hole 120 in each alignment tab. Finger rest 104 has a corresponding number of lips 122 and a plurality of alignment tabs 118 each with pin hole 120, such that when aligned, the pin holes are sufficiently aligned that pins 108 can be inserted through each of the pin holes. Pins 108 form axles that top wings 110 may pivot on, as will be explained further below. In other words, wings 110 pivot about a longitudinal axis A (as shown in FIG. 6A) rather than about a transverse axis B (orthogonal to axes A).

Top wings 110 have each have at least one alignment tab 124. Alignment tabs 124 each have pin hole 120 such that when alignment tabs 124 are positioned on finger rest 104, pin 108 is inserted through pin holes 120. Pin 108 acts similar to a hinge allowing top wings 110 to pivot about pin 108.

Figure 5:
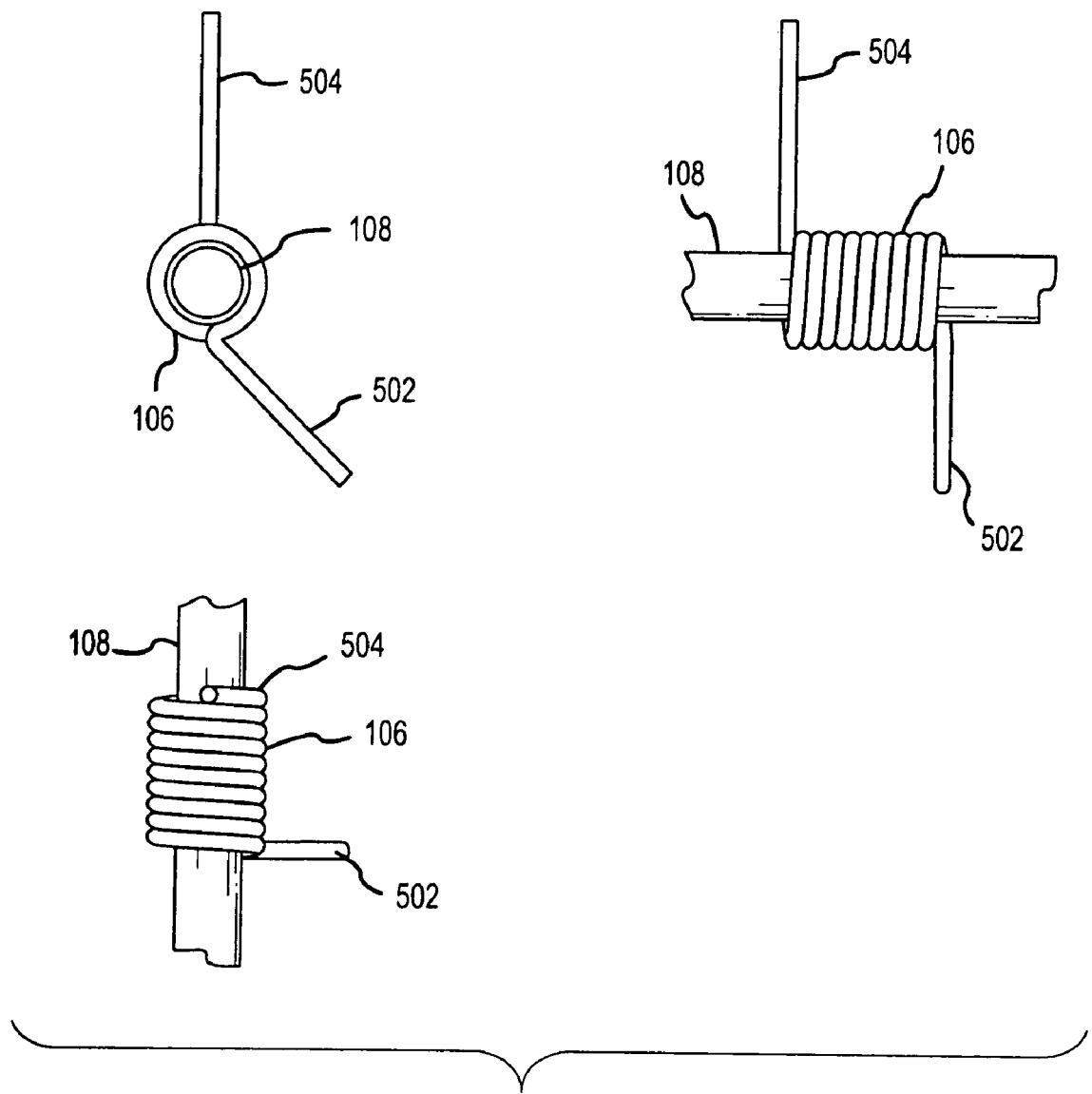
FIG. 5 is a side elevation view of a elastic biasing member associated with the biofeedback sensor of FIG. 1.
Figure 7:
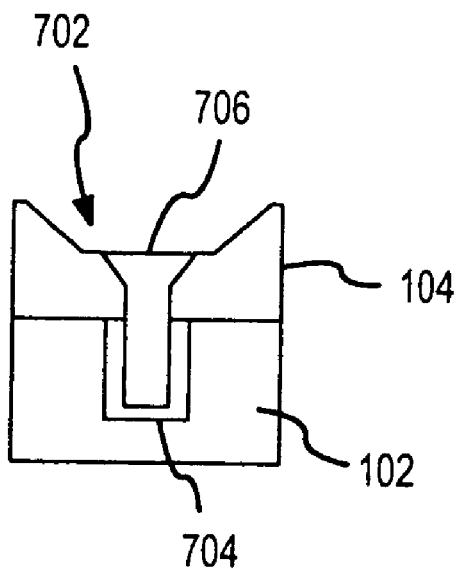
FIG. 7 is a cross-sectional view of another means for attaching the finger rest and bottom of FIG. 1.
Figure 8:
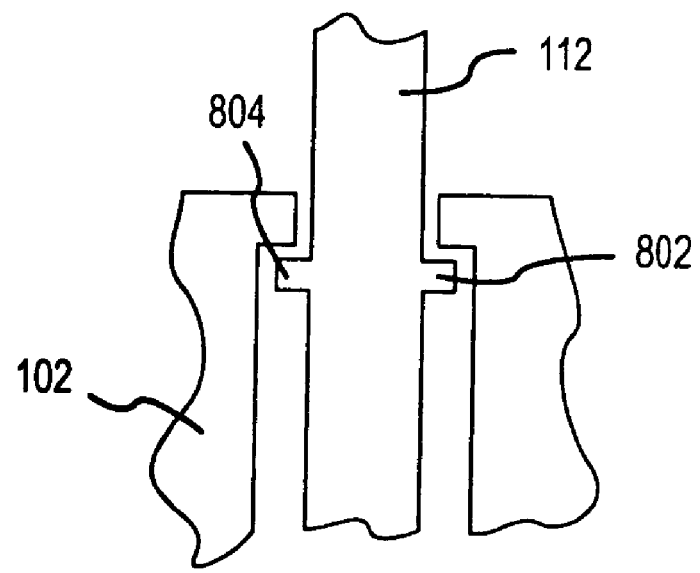
FIG. 8 is a cross-sectional view of still another means for attaching the finger rest and bottom of FIG. 1.

Elastic biasing members 106 are mounted on pins 108, as shown by FIG. 5. Elastic biasing member 106 has prongs 502 and 504. Prong 502 is substantially aligned with finger rest 104 or bottom 102 while prong 504 is substantially aligned with wing 110. Elastic biasing member 106 is generally under a compressive force, tending to cause wings 110 to pivot towards bottom 102. Thus, when placed on a finger, wings 110 pivot away from bottom 102 by the pressure associated with inserting a finger, but the compressive force associated with elastic biasing member 106 exerts a pressure tending to caused wings 110 to pivot towards bottom 102 causing a snug, but comfortable, fit on the finger of a client. Finally, while shown as a coil spring for convenience, one of ordinary skill in the art would recognize that other tension or compression members would be equally useful, such as, for example, spring steel, plastic composites with sufficient elasticity, or the like. Basically, the elastic biasing member simply needs to supply sufficient force that wings 110 seat snuggly, but not uncomfortably, on the appendage of the client. While a number of torque values are possible, it has been found that biasing member 106 works well if the torque value is between 200 and 600 gf. For the specific design shown where the covers portions 202 and 204 are specifically contoured, it has been found that having different biasing values for each member provides a snug fit on the appendage. In this case, the torque value for the right biasing member would be in the range of about 350 gf to 400 gf and more preferably 360 gf. The torque value for the left biasing member would be a greater torque and in the range of 450 gf to 500 gf and more preferably about 460 gf.

Bottom 102 (or finger rest 104) has a recess 130. If recess 130 is in bottom 102, finger rest 104 has an opening 132 or window substantially aligned with recess 130. An electrode 126 or infrared sensor 128 resides in recess 130 having an electrical cable coupled to connector 134 or wireless transmitter 136 to transmit the biofeedback signal to a processor (not shown). Opening 132 in finger rest 104 allows sensor, which could be, for example, infrared sensor 128 to sensor biometrics from a finger or other appendage resting on finger rest 104.

Figure 2A:
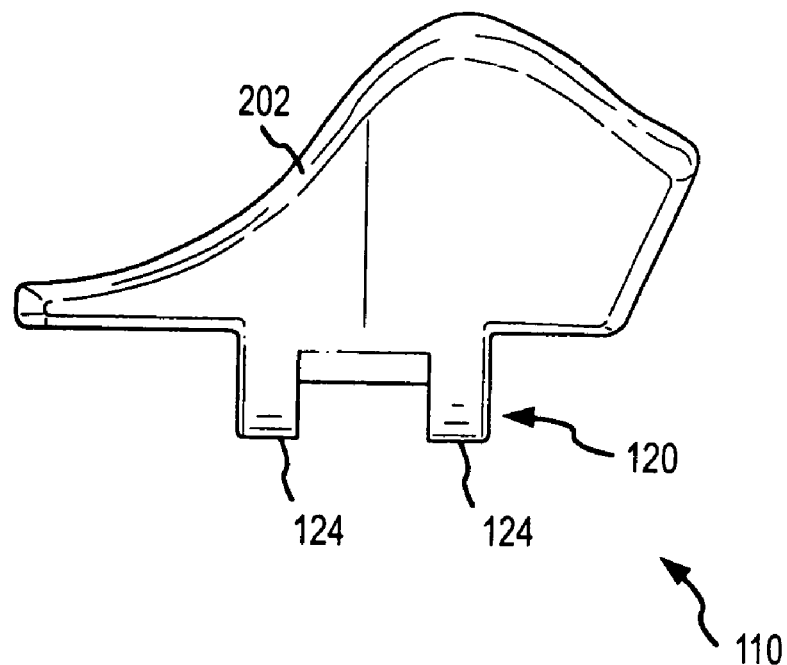
FIGS. 2A and 2B are side elevation views of wings associated with the biofeedback sensor of FIG. 1.
Figure 2B:
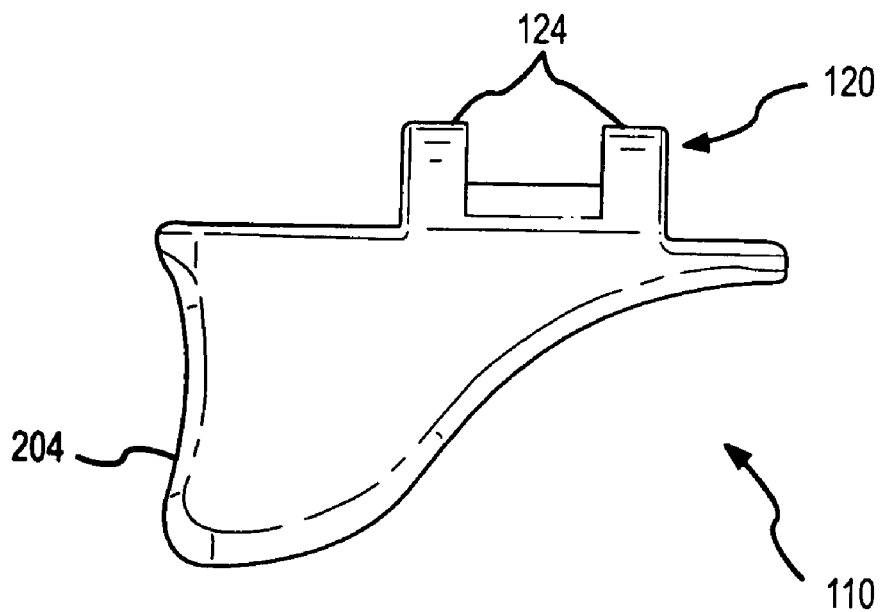

FIG. 2A shows a side elevation view of a wing 110. As described above, wing 110 has alignment tabs 124 with pin holes 120. Wing 110 pivots about pin 108 that would extend between alignment tabs 124. FIG. 2B shows a side elevation view of the other wing 110. Wings 110 have cover portions 202 and 204 designed to fold together over, for example, a finger. While wings 110 could have identical shapes, individually contouring each cover portion 202 and 204 allows better fit. For example, cover portions 202 and 204 are contoured to fit the ring, middle, and index finger of a client. Other contours are possible to fit other appendages as desired. FIG. 6C shows how cover portions 202 and 204 fit together in more detail.

Figure 3A:
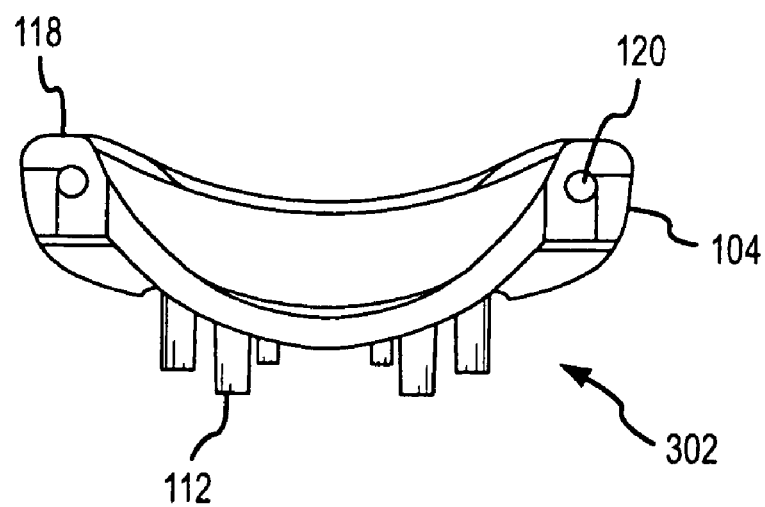
FIG. 3 is a top plan view of a finger rest associated with the biofeedback sensor of FIG. 1.
Figure 3B:
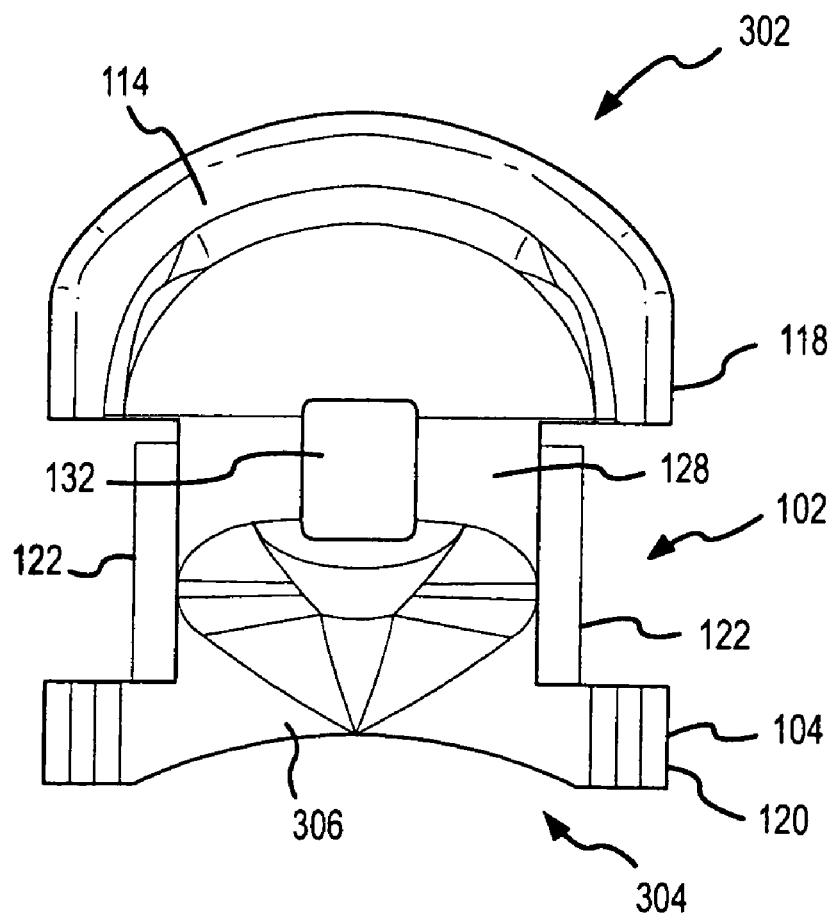

Referring now to FIGS. 3A and 3B, a top plan view (FIG. 3B) and a front elevation view (FIG. 3A) of finger rest 104 is shown. In FIG. 3B, bottom 102 is partially shown below finger rest 104. Finger rest 104 is designed with a rounded front end 302 and an open back end 304. While front end 302 is shown rounded, it could have other shapes, but it is believed a rounded end fits best with, for example, a finger where ring type biometric sensors are typically located on a client. A resting surface 306 has a concave shape generally contoured to the shape of an appendage, such as a finger or toe. If, for example, an index finger were resting on finger rest 104, the tip of the client's finger (or distal end of an appendage) would be placed substantially adjacent or abutting rounded front end 302. The knuckle end of the client's finger (or proximate end of an appendage) would extend out the open back end 304. The finger print part of the index finger (or corresponding part of another appendage) would reside substantially aligned with opening 132. Sensor, for example, infrared sensor 128 in recess 130 of bottom 102 would thus be proximate the appropriate part of the client's finger (or other appendage) to read the appropriate biometric information, such as, for example, blood oxygen levels, pulse, or the like.

Figure 4:
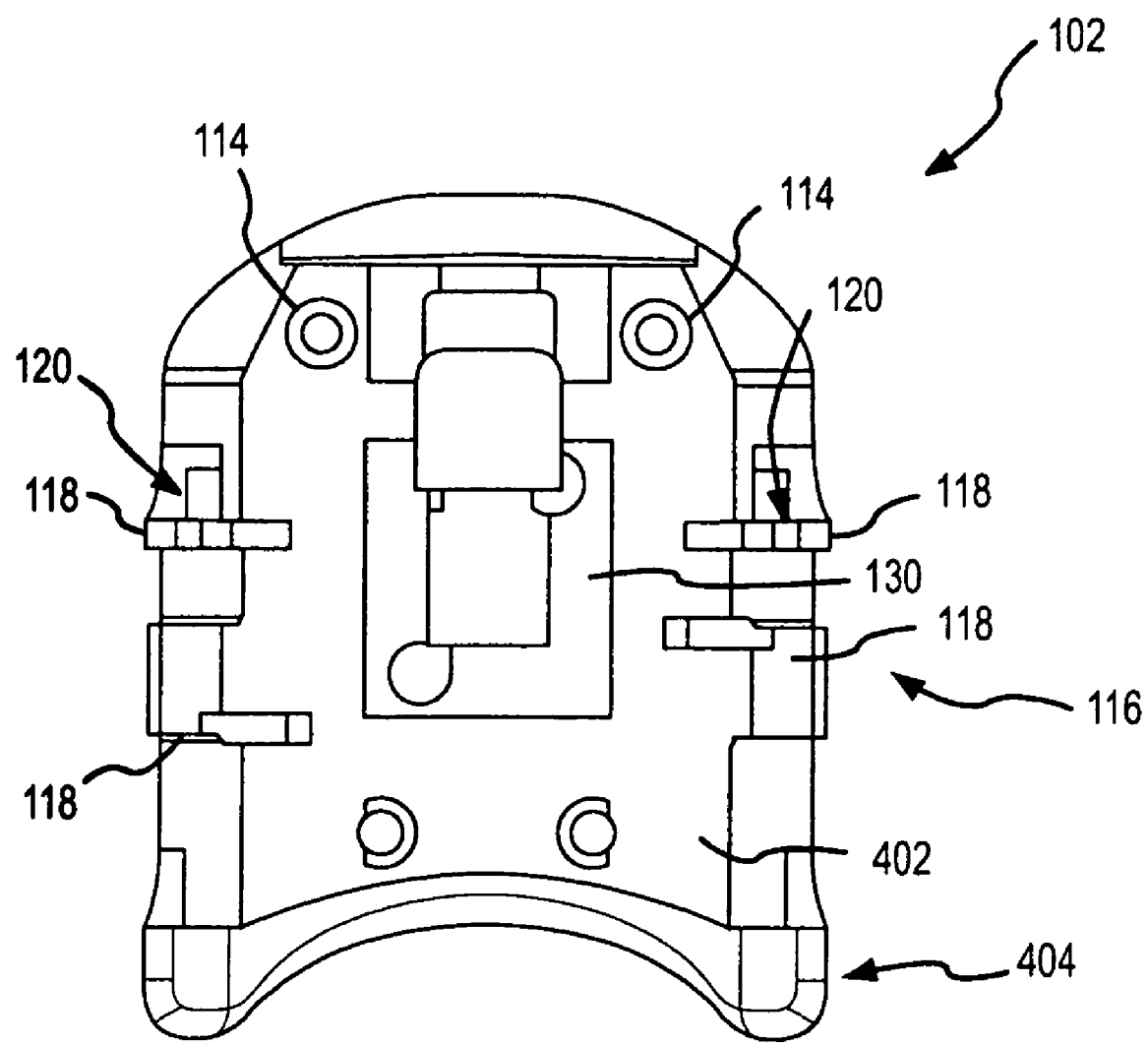
FIG. 4 is a top plan view of a bottom associated with the biofeedback sensor of FIG. 1.

Referring now to FIG. 4, a top plan view of bottom 102 is shown. Bottom 102 has a concave lower surface 402 in which finger rest 104 resides. Bottom 102 has an outer surface 404. Outer surface 404 is shown as rounded to more conform to the appendage of a client, such as a client's finger, but could be flat or other shapes as a matter of design choice. Concave lower surface 402 contains recess 130, unless recess 130 is designed into finger rest 104, in which case finger rest 104 would not need opening 132.

Bottom 102 has shoulders 116. Extending from shoulders 116 are alignment tabs 118. The lips 122 of finger rest 104 may rest on shoulders 116 such that pin holes 120 in the alignment tabs 118 align sufficiently that pins 108 may be inserted through pin holes 120.

Pegs 112 of finger rest 104 are placed in holes 114 of bottom 102 to hold finger rest 104 in place. Notice, instead of a frictional engagement, pegs 112 could have a protrusion 802 and holes 114 could have a shoulder 804 such that pegs 112 and holes 114 form a snap-lock (see FIG. 8).

Referring now to FIGS. 6A to 6C, a top plan, side elevation, and front elevation view of sensor 100 is provided. FIG. 6A shows how cover portions 202 and 204 of wings 110 fit together to form a snug enclosure 602 for an appendage of the client, such as, in this case, a finger. As best seen in FIG. 6C, covers 202 and 204 and front end 302 are contoured to fit a finger and could have alternative shapes to fit different appendages or for aesthetic reasons. FIG. 6C also best shows pin 108 inserted into pin holes 120 to allow wings 110 to pivot. Elastic biasing members 106 (not shown in FIG. 6) cause wings 110 to "clamp" around a finger or other appendage of the client to form a snug fit. As shown best in FIG. 6B, bottom 102 also is contoured to generally match the contour of the appendage, but bottom 102 could have alternative configurations, such as, flat, rounded, elliptical, random, or the like and the shape of bottom 102 is largely a matter of design choice. Because wings 110 "clamp" down on, for example, a finger, they may be constructed out of a plastic or have a pad 138 attached to rest on the finger. Pad 138 may be a foam or gel layer that conforms more to the finger (or appendage) than, for example, a stiffer plastic or metal.

While the invention has been particularly shown and described with reference to an embodiment thereof, it will be understood by those skilled in the art that various other changes in the form and details may be made without departing from the spirit and scope of the invention.

We claim:

1. A biofeedback measuring apparatus, comprising:
   an appendage rest;
   at least one sensor;
   the at least one sensor coupled to the apparatus such that when an appendage of a client is in the appendage rest, the at least one sensor can measure biometric information; and
   a plurality of wings, each of the plurality of wings traversing a longitudinal axis of the appendage rest;
   the appendage rest and the plurality of wings defining an enclosure having an enclosure top formed by the plurality of wings traversing the longitudinal axis of the appendage rest and an enclosure bottom formed by the appendage rest adapted to fit an appendage of a user;
   a plurality of elastic biasing members coupled to the plurality of wings and the appendage rest; and
   the plurality of wings pivotally coupled to the appendage rest such that the plurality of wings pivot about the longitudinal axis such that the plurality of elastic biasing members are adapted to provide a clamping force about and down on the appendage to contain the appendage in the appendage rest and the plurality of wings.

2. The apparatus of claim 1, further comprising:
   a bottom, the bottom coupled to the appendage rest;
   at least one recess located in the bottom for holding the at least one sensor; and
   wherein the appendage rest includes at least one opening substantially aligned with the at least one recess.

3. The apparatus of claim 1, wherein
   the plurality of elastic biasing members comprise springs.

4. The apparatus of claim 3, wherein
   the springs are selected from a group of springs consisting of coiled springs, leaf springs, spiral springs, and helical springs.

5. The apparatus according to claim 3 wherein the springs comprise spring steel.

6. The apparatus of claim 1, wherein the plurality of elastic biasing members comprise plastics.

7. The apparatus of claim 1, wherein the appendage rest is contoured to a shape to fit the appendage of the client.

8. The apparatus of claim 1, wherein the wings have at least one cover portion contoured to a shape to fit the appendage of the client.

9. The apparatus of claim 8, wherein the appendage rest is contoured to the shape to fit the appendage of the client such that the enclosure is generally the shape of the appendage.

10. The apparatus of claim 9, wherein the shape is the shape of a finger.

11. The apparatus of claim 1, wherein the appendage rest further comprises:
    a recess on a lower surface; and
    the sensor resides in the recess.

12. The apparatus of claim 1, further comprising a plurality of pads corresponding to the plurality of wings such that each of the plurality of wings has a pad between the wing and the appendage of the client.

13. A biofeedback apparatus, comprising:
    a bottom,
    the bottom having a recess;
    a sensor residing in the recess;
    the bottom having at least one shoulder;
    the bottom having at least one bottom alignment tab projecting from the at least one shoulder, the at least one bottom alignment tab having at least one bottom pin hole;
    an appendage rest,
    the appendage rest having at least one lip and at least one rest alignment tab, the at least one rest alignment tab having at least one rest pin hole, such that when the at least one lip abuts the at least one shoulder the at least one bottom alignment tab and the at least one rest alignment tab are arranged such that the at least one bottom pin hole and the at least one rest pin hole are aligned;
    at least two wings, each of the at least two wings traversing a longitudinal axis;
    the at least two wings each having at least one cover and at least one wing alignment tab with at least one wing pin hole;
    the appendage rest and the at least two wings defining an enclosure, the enclosure having an enclosure top formed by the at least two wings traversing the longitudinal axis and an enclosure bottom formed by the appendage rest; and
    at least two pins, wherein
    each of the at least two wings are pivotally coupled to the bottom and the appendage rest by aligning the at least one wing alignment tab with the at least one bottom alignment tab and the at least one rest alignment tab such that the at least one wing pin hole, the at least one rest pin hole, and the at least one bottom pin hole align, one of the at least two pins being inserted therethrough, such that the at least two wings pivot about the longitudinal axis, wherein
    the appendage rest and the at least two wings form the enclosure to enclose an appendage of a client and the at least two wings are adapted to provide a clamping force about and down on the appendage to retain the appendage in proximity to the sensor such that the sensor can obtain biometric information from the appendage through the opening in the appendage rest.

14. The apparatus of claim 13, further comprising:
    at least two elastic biasing members;
    the at least two elastic biasing members coupled to the at least two pins and providing pivotal force to the at least two wings.

15. The apparatus according to claim 14, wherein the at least two elastic biasing members are springs.

16. The apparatus according to claim 13, wherein the appendage rest and the at least two wings are contoured to conform to the appendage of the client.

17. The apparatus according to claim 13, further comprising at least one pad coupled to the at least two wings such that the at least one pad resides between the at least two wings and the appendage of the client.

18. The apparatus of claim 13, wherein
    the bottom comprises a plurality of holes;
    the appendage rest comprises a plurality of pegs, wherein when the bottom and the appendage rest are coupled together, the plurality of pegs reside in the plurality of holes.

19. The apparatus of claim 18, wherein the plurality of pegs and the plurality of holes form a frictional engagement.

20. The apparatus of claim 18, wherein each of the plurality of holes comprises at least one shoulder, and each of the plurality of pegs comprise at least one lip, such that the plurality of holes and plurality of pegs form a snap lock.

21. The apparatus of claim 13, wherein the bottom further comprises a plurality of threaded holes and the appendage rest comprises a corresponding plurality of through holes, further comprising a plurality of threaded members extending through the plurality of through holes and threaded into the plurality of threaded holes to couple the bottom and the appendage rest together.

22. A biofeedback measuring apparatus, comprising:
an appendage rest;
at least one sensor;
the at least one sensor coupled to the apparatus such that when an appendage of a client is in the appendage rest, the at least one sensor can measure biometric information;
at least two wings, each of the at least two wings traversing a longitudinal axis of the appendage rest;
the appendage rest and the at least two wings defining an enclosure adapted to receive an appendage having an enclosure top formed by the at least two wings traversing the longitudinal axis of the appendage rest and an enclosure bottom formed by the appendage rest;
at least one elastic biasing member coupled to each of the at least two wings and the appendage rest; and
the at least two wings pivotally coupled to the appendage rest so the at least two wings pivot about the longitudinal axis and such that the at least one elastic biasing member is adapted to provide a clamping force about and down on the appendage to contain the appendage in the appendage rest and the at least two wings.

23. The apparatus of claim 22, further comprising:
a bottom, the bottom coupled to the finger rest;
at least one recess located in the bottom for holding the at least one sensor; and
wherein the appendage rest includes at least one opening substantially aligned with the at least one recess.

24. The apparatus of claim 22, wherein the at least one biasing member coupled to each of the at least two wings provides a compressive force.

25. The apparatus of claim 24, wherein the compressive force is about 200 gf to about 600 gf.

26. The apparatus of claim 25, wherein the compressive force is about 350 gf to about 500 gf.

27. The apparatus of claim 22, wherein a first of the at least one biasing member provides a compressive force in the range of about 450 to 500 gf.

28. The apparatus of claim 22, wherein a first of the at least one biasing member provides a compressive force in the range of about 350 to 400 gf.

29. The apparatus of claim 28, wherein a second of the at least one biasing member provides a compressive force in the range of about 450 to 500 gf.

30. The apparatus of claim 29, wherein the first of the at least one biasing member provides a compressive force of about 360 gf and the second of the at least one biasing member provides a compressive force of about 460 gf.

31. A system for measuring biometric information of a user comprising:
a plurality of rings, each ring comprising:
means for enclosing an appendage of a user having a bottom formed by an appendage rest and a top formed by at least two covers pivotally connected to the appendage rest, the at least two covers traversing a longitudinal axis of the appendage rest and connected to pivot about the longitudinal axis of the appendage rest;
means for causing the at least two covers to hold an appendage of the user in the appendage rest by providing a clamping force about and down on the appendage;
a plurality of sensors, wherein at least one of the plurality of sensors is coupled to a corresponding one of the plurality of rings; and
wherein each of the plurality of sensors measures biometric information.

32. The system of claim 31, wherein at least one of the plurality of sensors is different from the others of the plurality of sensors.

33. The system of claim 31, wherein at least one of the plurality of sensors is an infrared sensor.

34. The system of claim 31, wherein at least two of the plurality of sensors are electrodes that are used in combination to measure epidural skin response.

35. The system of claim 31, wherein the means for causing the at least two covers to hold an appendage of the user in the appendage rest comprises a spring.

* * * * *